(12) United States Patent
Jiang et al.

(10) Patent No.: US 6,905,831 B2
(45) Date of Patent: Jun. 14, 2005

(54) REAL TIME MEASUREMENT OF CELLULAR RESPONSES

(75) Inventors: Ping Jiang, San Diego, CA (US); Mingxu Xu, La Jolla, CA (US); Meng Yang, San Diego, CA (US)

(73) Assignee: Anticancer, Inc., San Diego, CA (US)

( * ) Notice: Subject to any disclaimer, the term of this patent is extended or adjusted under 35 U.S.C. 154(b) by 0 days.

(21) Appl. No.: 10/643,785

(22) Filed: Aug. 18, 2003

(65) Prior Publication Data

US 2004/0115813 A1 Jun. 17, 2004

Related U.S. Application Data

(60) Provisional application No. 60/404,005, filed on Aug. 16, 2002, and provisional application No. 60/427,604, filed on Nov. 18, 2002.

(51) Int. Cl.$^7$ .................................................. C12Q 1/68
(52) U.S. Cl. ............................ 435/6; 435/455; 435/366
(58) Field of Search ............................ 435/6, 455, 366

(56) References Cited

PUBLICATIONS

Gerdes and Kaether, FEBS Letters 389:44–47 (1996).
Kanda et al., Curr. Biol. 8:377–385 (1998).
Kawakami et al., Immunology Lett 70:165–171 (1999).
Yang et al., Clin. Exp. Metastasis 17:417–422 (1999).
Yang et al., Proc. Natl. Acad. Sci. USA 97:1206–1211 (2000).
Yang et al., Proc. Natl. Acad. Sci. USA 97:12278–12282 (2000).
Yang et al., Proc. Natl. Acad. Sci. USA 98:2616–2621 (2001).
Yang et al., Proc. Natl. Acad. Sci. USA 99:3824–3829 (2002).
Zhao et al., Proc. Natl. Acad. Sci. 98:9814–9818 (2001).
International Search Report, mailed on Feb. 11, 2004, for PCT/US03/22308, 4 pages.
Terjung et al., Clin. Exp. Immunol. (2001) 126:37–46.
Zhai et al., J. Biol. Chem. (2001) 276(44):41318–41324.
Zhang et al., J. Cell Sci. (2001) 114(24):4485–4498.

*Primary Examiner*—James Ketter
(74) *Attorney, Agent, or Firm*—Morrison & Foerster LLP

(57) ABSTRACT

Living cells can be stably modified to emit different colors from the cytoplasm and nucleus, thus permitting analysis of the status of said cells and the effect of agents on said cells either by visual or instrumentally-aided observation. These observations may be made, if desired, in real time. In addition, rates of proliferation and drug sensitivities can be determined in vitro in real time by the use of cells modified to express a single fluorescent protein and observing fluorescence intensity as a function of time.

27 Claims, 13 Drawing Sheets

PC-3 Dual Cells were treated by Taxol (0.8 µg/ml)

T0 (Magnification:200x)

T24 (Magnification:200x)

T48 (Magnification:200x)

T96 (Magnification:200x)

*Visualizing taxol induced apoptotic cells in vitro in real time*

Real-time apoptoses were observed under fluorescence microscopy and verified by DNA ladder analysis when PC-3-dual cells were incubated with 0.8 μg Taxol. (A) control; (B) 12 hours after treatment; (C) 24 hours after treatment; (D) 36 hours after treatment; (E) 48 hours after treatment.

PC-3 Dual Cells were treated by Vinblastin (62μg/ml)

T0 (Magnification:200x)

T96 (Magnification:200x)

T0 (Magnification:200x)

T48 (Magnification:200x)

Visualizing apoptotic cancer cells in vivo

PC-3 Dual colored human prostate cancer cells were injected in the foot pat of nude mice. The mice were sacrificed after 20 days. Apoptotic PC-3 dual colored cell was observed in the lymph node under fluorescence microscopy

REAL TIME MEASUREMENT OF CELLULAR RESPONSES

CROSS-REFERENCE TO RELATED APPLICATIONS

This application claims priority under 35 U.S.C. § 119(e) from U.S. Ser. Nos. 60/427,604 filed 18 Nov. 2002 and 60/404,005 filed 16 Aug. 2002, the contents of which are incorporated herein by reference.

TECHNICAL FIELD

The invention relates to real time observation of cellular proliferation, drug sensitivity, cell cycle position, and other cellular responses in vitro. The invention relates to direct observation of cells, especially living cells, by use of fluorescent proteins as markers. The status of cells in a cell cycle can be monitored by separately labeling the nucleus and cytoplasm.

BACKGROUND ART

The green fluorescent protein (GFP) from Aequorea victoria was discovered in 1962. Knowledge of the structure, mechanism and applications of GFP developed very rapidly after cloning of the GFP gene in 1992. After demonstration of the heterologous expression of the GFP gene in other organisms, GFP became one of the most widely used reporter genes. In 1999, another family of fluorescent proteins, including Discosoma Red (DsRed), was cloned from corals followed by Anemonia asRed in 2000 and HcRed in 2001. The biological role of these proteins extends from a pure signal function as in GFP to photoprotection of photosynthetic symbionts by the novel proteins isolated from corals. For two of these colored, water-soluble proteins, GFP and DsRed, with a molecular weight of 25–27 kD, X-ray structure analysis has demonstrated a homologous β-barrel structure. A common feature of the primary structure of these proteins is that the amino acids, tyrosine and glycine, which occupy GFP positions 66 and 67, are conserved and participate in the formation of the chromophore during a post-translational autocatalytic modification.

These proteins (wild type and mutants) can be used as multicolor reporters. The spectral range of their fluorescence spans almost 180 nm extending from the "blue" peak position of 460 nm to 640 nm in the red region of the spectrum. GFP is one of the most widely-used genetic markers in cell biology (Gerdes, H.-H., and Kaether, C., *FEBS Letters* (1996) 389:44–47), in immunology (Kawakami, N., et al., *Immunology Lett* (1999) 70:165–171), as well as in studies of infectious disease, e.g.—of host-pathogen interaction on model animals (Zhao, M., et al., *Proc. Natl. Acad. Sci.* (2001) 98:9814–9818). GFP has been used for whole-body imaging of tumor growth, metastasis, and angiogenesis (Yang, M., et al., *Proc. Natl. Acad. Sci.* (2002) 99:3824–3829; Yang, M., et al., *Proc. Natl. Acad. Sci. USA* (2000) 97:1206–1211; and Yang, M., et al., *Proc. Natl. Acad. Sci. USA* (2001) 98:2616–2621), gene expression (Yang, M., et al., *Proc. Natl. Acad. Sci. USA* (2000) 97:12278–12282), and bacteria infection (Zhao, M., et al, supra).

In all these applications, the red emission is of special importance with respect of minimization of background emission and in vivo scattering as well as for FRET (fluorescence resonance energy transfer) analysis. High extinction coefficients, quantum yield, and the monomeric state of fluorescent proteins are very important parameters for their use as reporters including in vivo applications. In contrast to GFP, which has only a small tendency to dimerize, the related proteins have a pronounced tendency to form oligomers, e.g.—tetramers as observed for DsRed, or even higher aggregates. Extinction coefficients and quantum yields are also relatively low for red proteins and for the newly developed monomeric DsRed.

The human histone H2B gene has been fused to the gene encoding the GFP of *Aequorea victoria* and transfected into human cells to generate stable lines constitutively expressing H2B-GFP. The H2B-GFP fusion protein was incorporated into nucleosomes without affecting cell cycle progression. H2B-GFP allowed high-resolution imaging of nuclei including both mitotic chromosomes and interphase chromatin, and the latter revealed various chromatin condensation states in live cells (Kanda, T., et al., *Curr. Biol.* (1998) 8:377–385).

The disclosures of the cited documents are incorporated herein by reference.

These various proteins have been used to monitor tumor metastases, and as reporter genes to monitor expression. See, for example, Kanda, T., et al., *Curr. Biol.* (1998) 8:377–385; Yang, M, et al., *Clin. Exp. Metastasis* (1999) 17:417–422; Yang, M, et al., *Proc. Natl. Acad. Sci. USA* (2001) 98:2616–2621; and Yang, M, et al., *Proc. Natl. Acad. Sci. USA* (2002) 99:3824–3829. However, to applicants' knowledge, these proteins have not been used to monitor cellular proliferation, cell cycle status, or drug sensitivity of cells in vitro, nor have dual labeled cells been used either in vitro or in vivo.

Most in vitro techniques for monitoring proliferation involve observation techniques which results in killing the cells. For example, cells that proliferate attached to a plastic surface may be released from the plastic by enzymes, such as trypsin, and then counted using a particle counter. Also commonly employed are stains such as tetrazolium dyes which are reduced by electrons derived from mitochondrial enzyme activity and negatively affect the viability of the cells. In addition, the lacZ gene may be introduced into the cells and used as a marker, but in order to visualize activity, the cells must be stained.

Thus, traditional methods of monitoring proliferation involve disruption of normal cellular metabolism, even resulting in cell death.

The present invention offers an opportunity to observe proliferation and other cellular activity in vitro or in vivo in real time. These observations may also extend to observing the cell cycle by taking advantage of changes in nuclear/cytoplastic ratios at various stages.

To applicants knowledge, although the H2B gene fused to GFP has been used to label the nucleus, no suggestion has been made to separately label the nucleus and cytoplasm of living cells with two different color proteins. The present invention provides the capability to observe such living cells.

DISCLOSURE OF THE INVENTION

The present invention is directed to methods for observing proliferation and sensitivity of cells to various compounds in vitro and in vivo. In addition, the invention is directed to dual labeled cells where one color is used to label the nucleus and a different color to label the cytoplasm.

Thus, in one aspect, the invention is directed to a method to measure cellular proliferation in vitro which method comprises the step of observing, as a function of time, changes in intensity of fluorescence of cells in culture labeled with a fluorescent protein.

In another aspect, the invention is directed to monitoring the response of cells to compounds such as drugs in vitro by measuring, as a function of time, the fluorescence emitted by cell cultures in the presence and absence of test compound, wherein the cells in said cultures have been modified to express a fluorescent protein.

In still another aspect, the invention is directed to a method to label living cells by providing said cells with an expression system for a first fluorescent protein of a first color which remains in the cytoplasm, and an expression system for a second fluorescent protein coupled to a nuclear targeting protein wherein upon expression of said first protein and said second fusion protein, the nucleus of said cells is labeled with one color and the cytoplasm with a different color.

In another aspect, the invention is directed to cells thus prepared, which are stably labeled in the cytoplasm with a first fluorescent protein and in the nucleus with a second fluorescent protein of a different color from the first.

In other aspects, the invention is directed to methods of using the dual-labeled living cells obtained by the method of the invention either in culture or in a living plant or animal. The effect of various agents on the cell cycle can be determined using these cells as well.

BRIEF DESCRIPTION OF THE DRAWINGS

FIG. 3A is taken at five-minute intervals. a: 0 minute. b: 5 minutes. c: 10 minutes. d: 15 minutes. e: 20 minutes. f: 25 minutes. g: 30 minutes. Bars; 20 μm. FIG. 3B is taken at thirty-minute intervals. a: 0 minute. b: 30 minute. c: 60 minutes. d: 90 minutes. e: 120 minutes. Bars; 75 μm. Green and white circles indicate representative areas where proliferating cells were observed. Even if mitotic cells changed their relative positions, they were easily visualized.

FIG. 4A shows an image twelve hours after 2 μM staurosporine treatment. Apoptosis was well induced to HT-1080-dual cells at a high rate. Bar, 50 μm. FIG. 4B shows real-time high-magnification images of HT-1080-dual-6 cells apoptotic processes induced by 2 μM staurosporine as follows: a: no treatment. b: 2 hours after staurosporine treatment. c: 4 hours. d: 6 hours. e: 8 hours. f: 10 hours. g: 12 hours. The condensation of cytoplasm and nucleus and fragmentation of nucleus were well visualized. Bar, 10 μm.

FIG. 5A is a low magnification view. Bar, 400 μm, the white square indicates the area whose high magnification view is shown in FIG. 5B. FIG. 5B shows a high magnification view. Bar, 100 μm.

FIG. 6A shows a high magnification image. Bar, 50 μm. FIG. 6B is a schema of FIG. 6A.

MODES OF CARRYING OUT THE INVENTION

Figure 1:
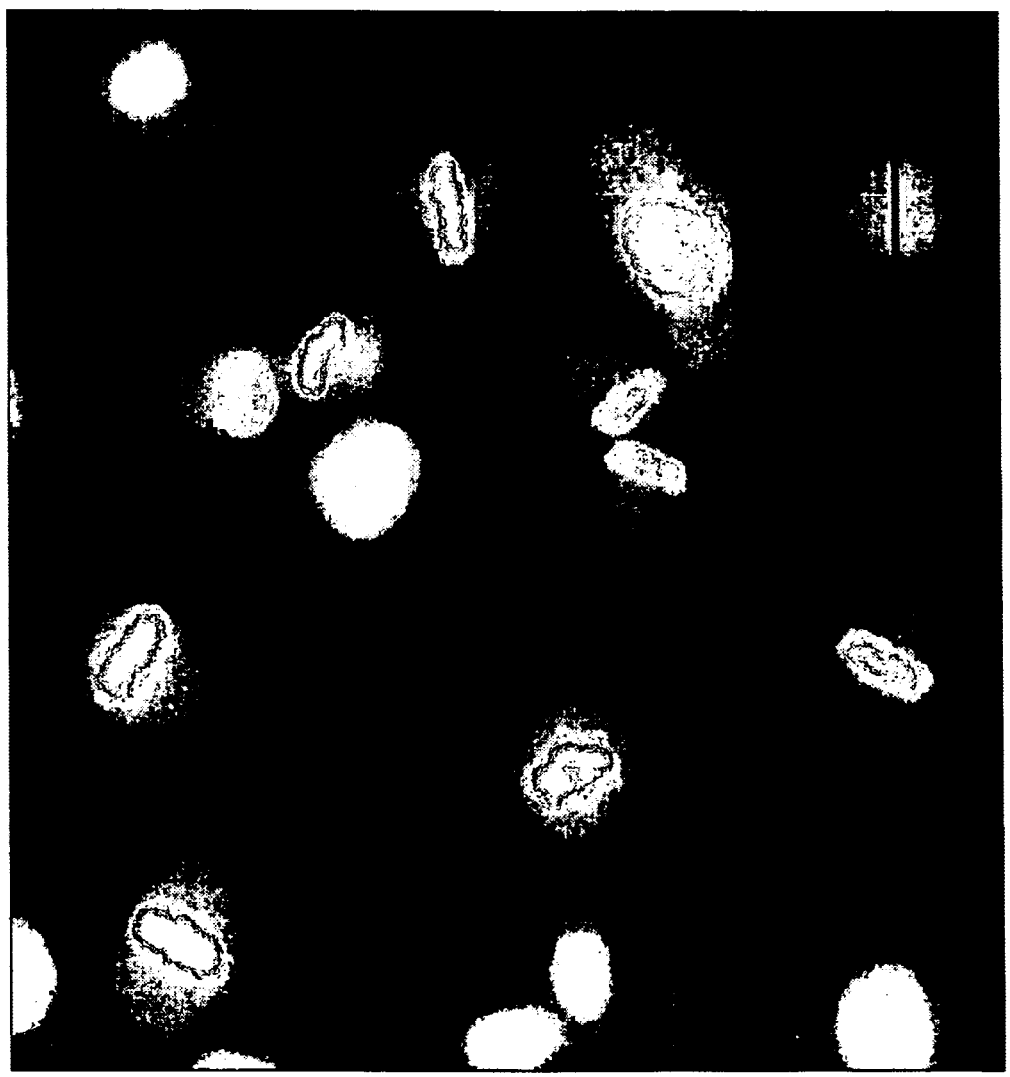
FIG. 1 shows stable high GFP and RFP expressing human fibrosarcoma cells (HT-1080-dual-1) in vitro. Human fibrosarcoma cells (HT-1080) were transduced with RFP and the neomycin resistance gene, histone H2B-GFP and the hygromycin resistance gene in a retrovirus vector. Double transformants were selected with G418 and hygromycin and stable clones were established. Bar, 50 μm.

Enhancement of information obtainable by cellular labeling can be obtained by separately labeling the nucleus and cytoplasm. Such dual labeling permits not only monitoring of cell proliferation, but also monitoring of events in cellular life. Particularly convenient are the labels of the invention wherein the nucleus is labeled with one color emitted as fluorescence and the cytoplasm is labeled with another color.

Also a feature of the invention are methods for monitoring proliferation of cells in vitro or in vivo in real time simply by monitoring fluorescence. While the dual labeled cells may be used in this method, dual labeling is not strictly speaking necessary. Cells labeled with only a single fluorescent label whose intensity can be measured while the cells remain alive can be used. The response to various treatments or drugs can also be monitored in this way by ascertaining the effect of the drug or agent on cellular proliferation.

Suitable cells for use in the invention are cells of any eukaryotic organism, such as yeast, fungi, plants, vertebrate and invertebrate animals, including human cells. For observation of unicellular organisms such as yeast and, for example, molds or fungi, direct observation in culture is preferred. Observation in cell culture may also be employed for cells of higher plants and animal cells. Suitable animals include, typically, laboratory animals such as rats, mice and other rodents, domestic animals such as livestock, fish, and human cells.

For methods of the invention which do not require dual labeling of the cytoplasm and nucleus, procaryotic cells may be used in addition to the eukaryotes discussed above.

The cells are labeled, according to the methods of the present invention, with fluorescent proteins. As used herein, a "fluorescent protein" refers to a protein that, upon appropriate stimulation, will emit light. Typically, a fluorescent protein emits light in the visible range—i.e., in the range of about 400 nm–800 nm, when illuminated with an excitation wavelength. When instrumentation is employed a wider range may be used. Other mechanisms for evoking fluorescence can also be used; a convenient example is that of luciferase, where metabolic energy is used to effect signal generation. Thus, a "fluorescent protein" refers to a protein which will emit light in the "visible" range when appropriate energy is supplied, whether by excitation radiation, chemiluminescence, or other mechanisms of supplying the necessary energy to effect light emission.

In many embodiments of the invention, fluorescent proteins, such as those described in the Background section above, are employed. As is apparent, these fluorescent proteins come in a variety of colors; in some notations, the color is included in the acronym for the protein—such as GFP for green fluorescent protein and RFP for red fluorescent protein. However, since the originally isolated fluorescent protein was green, in some instances the acronym GFP is used generically to describe these fluorescent proteins regardless of the wavelength emitted. Thus, in one sense, GFP can emit light in the yellow, red or blue wavelength range, for example. It will be clear from the context whether the generic meaning of GFP is used or whether it is intended that the emission be in the green wavelengths. For example, in illustrative embodiments, a red fluorescing protein is used to label the cytoplasm and a green fluorescing protein to label the nucleus. In notating these cells, GFP really means emission of green wavelengths and RFP emission of red wavelengths.

The invention provides methods for observing proliferation of, and determining proliferation rates of, cells in vitro or in vivo by means of observing the intensity of emitted fluorescence as a function of time. Clonal heterogeneity can also be determined using this technique.

Methods for obtaining transformed cells that produce fluorescent proteins are by now well known in the art. A wide variety of colors of fluorescence is available and stable cell lines have been produced as described, for example, in U.S. Pat. No. 6,232,523, incorporated herein by reference. In one embodiment of the present invention, these cells, rather than being observed in vivo, are employed in a real time in vitro assay.

In one embodiment, cancer cell lines stably expressing a fluorescent protein, such as GFP, are plated into 96-well dishes. At periodic time points, the plates are measured for fluorescence in each well in a fluorescence plate reader such as Molecular Devices Gemini. In each particular well, as the cells proliferate, the intensity of the fluorescence increases. Thus, the rate of proliferation can be read directly by plotting or otherwise manipulating the data of fluorescence intensity versus time.

For use to test the effects of various agents on the proliferation of cells, the wells of the plates are marked such that one set of wells serves as a control and other sets are incubated with drugs of interest. Plates are read for fluorescence intensity in each well at appropriate time intervals, typically either every day or every two days to obtain growth curves for control and drug-treated wells. The cultures need no treatment or additions for these measurements. Since GFP does not fluoresce after being hydrolyzed in dying apoptotic or necrotic cells, the GFP is an instant marker of cell viability. Total fluorescence in each well correlates with the number of living cells present allowing quantification. Accordingly, the ability of the test compounds to inhibit or to enhance proliferation can readily be determined.

In one application of the foregoing procedures, each well may be supplied with a minimal number of cells, or even a single cell, derived from a tumor. In this manner, tumor heterogeneity may be accounted for by employing the invention methods. The heterogeneity is observed by differences obtained among the wells, each representing the proliferation of one or a small quantity of cells obtained from the tumor.

The invention also provides stably transformed cells which express markers for the cytoplasm and nucleus. By supplying living cells with an expression system for a fluorescent protein lacking a nuclear targeting signal, and with an expression vector comprising a nucleotide sequence encoding a fusion protein wherein a second fluorescent protein of a different color is coupled to a nuclear targeting sequence, both the nucleus and the cytoplasm will be separately visible under microscopic observation. By thus dual labeling the cells, events in the cell cycle can conveniently be monitored and the effect of various agents on the cell cycle can also be evaluated. The cells may be directly observed under a microscope when in culture, or can be observed in an intact animal, even a living animal.

By "color" of the emitted light is meant the wavelength at which the light is emitted. The nucleus and the cytoplasm must emit light at different wavelengths which can be separately determined, and are thus designated as "different colors." The difference in color need not necessarily be detectable by the naked eye; although it is preferable that this level of difference in wavelength be present, it is also possible by using filters and/or detectors with different wavelength sensitivities to observe, with the aid of suitable software, even small differences in wavelength. Thus, for example, by the use of a wide field microscope, such as those described in U.S. Pat. No. 6,444,992, and incorporated herein by reference, differing wavelengths which are closely related can also be used.

It is, however, preferred to simplify observation by using fluorescent proteins whose color differences are detectable by the eye. Instrumentation is also simplified if wavelength differences are sufficient to permit visual differentiation.

Because the cells are stably transformed to produce the two fluorescent proteins, they can be observed while they are alive and undergoing the various stages of the cell cycle. The cells can be observed in culture, or can be observed while they are present in a living organism. For example, whole body observation in real time of living animals using cells stably transformed with green fluorescent protein is described in U.S. Pat. Nos. 6,251,384, 6,235,968 and 6,235,967 incorporated herein by reference . For use in whole organisms, proteins that are highly fluorescent are preferred; thus, only mildly fluorescent proteins such as luciferase are not practical when whole body observation is employed.

Of course, if foreign cells are implanted into laboratory animals, these animals must be sufficiently immunocompromised that the cells are not rejected. Techniques for immunocompromising a variety of animals are known in the art; convenient subjects which are already immunocompromised include nude or SCID mice and similarly modified other rodents such as rats.

The fluorescent proteins are any of those generally available in the art such as those described in the Background section hereinabove. A multiplicity of modifications of the originally isolated A. victoria green fluorescent protein has led to proteins with a variety of colors, and to proteins that are readily expressed in a wide variety of cell types. The options among fluorescent proteins of various emission wavelengths are many and are well known.

Any method of modifying the cells to be studied to contain the expression systems is suitable. The methods of transformation will depend on the nature of the cells and would include, for example, lipofection, electroporation, and viral infection, as a none-limiting list. For plant cells, Agrobacterium-mediated transformation can also be used, as well as modification of protoplasts. The choice of control sequences for the expression systems containing the nucleotide sequences encoding the proteins can also be varied and the choice of the appropriate controls and vectors will depend on the nature of the cells and the mode of cell modification.

Any suitable nucleus targeting signal can be used; exemplified below is the histone H2B; however, other sequences targeting the nucleus are known and could be substituted therefor.

Thus, the cells to be modified are transfected with a suitable vector comprising an expression system for each of the fluorescent proteins, one and only one of the fluorescent proteins being coupled to an additional amino acid sequence which will target that protein to the nucleus. The vectors used for transformation may be separate vectors for the fluorescent protein destined for the cytoplasm and the fluorescent protein of a different color destined for the nucleus or both expression systems can be contained on the same expression vector. The nuclear targeting sequence may be employed first, followed by transfection so that the cells contain the expression system for the fluorescent protein that will label the cytoplasm, preferably assuring the stability of the cell line between transfection events in order to assure stability. The order of transfection could also be reversed with the expression system for the cytoplasmic protein administered first. Alternatively, both expression vectors might be contacted with the cell simultaneously, preferably using different selection markers to assure co-transfection. It would also be possible to use a bicistronic expression system for both proteins.

In order to assure stable modification, including instances where the relevant expression systems may be integrated into the genome, the cells are subjected to selection pressure. Suitable selection markers will depend on the nature of the cells; G418 or hygromycin resistance is a convenient marker for a wide variety of cells; other alternative methods of selection include the use of a toxin such as methotrexate with respect to DHFR based systems. Those of ordinary skill will understand the type of selection to be employed.

Thus, in one approach, a suitable cell line is infected with a retroviral vector comprising an expression system wherein a nucleotide sequence encoding a fluorescent protein which emits blue light fused to an amino acid sequence encoding a nuclear targeting signal. The viral vector further contains hygromycin resistance as a selectable marker. The treated cells are then subjected to selection pressure in the presence of hygromycin and after several rounds of selection, stable transformants are obtained. The stably transformed cells are then treated with DNA using electroporation wherein the vector comprises green emitting fluorescent protein coupled to DHFR. The cells are subjected then to rounds of selection with both hygromycin and methotrexate to obtain a cell line wherein the nucleus is stained blue and the cytoplasm green.

The differential staining obtainable by the method of the invention is useful in view of the fact that various portions of the cell cycle give rise to different distributions and/or intensities of radiation emitted from the nucleus and the cytoplasm. Thus, for example, the ratio of intensities will permit determination of cell cycle position. In addition, the morphology of the nucleus is altered when apoptosis occurs and this can readily be detected. The effect of various agents, including various small molecule drugs, proteins, antisense or triplex forming nucleic acids or inhibitor RNA can be tested by observing the effects of these agents on the cellular cycle or morphology. Differential targeting of various agents to the cytoplasm or to the nucleus can also be observed using the methods of the invention. The characteristics of the cells that can be evaluated include dormancy, apoptosis, stage of cell cycle, location of targeting agents, and a multiplicity of other characteristics that will familiar to the artisan. If desired, agents used to treat the cells may themselves be labeled.

Thus, if the cells are to observed through a microscope in culture, the agent may be added directly to the culture. If the cells are to observed in a living animal or plant, the agent is typically administered directly to the animal or plant.

In one embodiment, cancer cells are doubly labeled with histone H2B-GFP expressed only in the nucleus and DsRed-2 introduced with a retroviral vector that is expressed solely in cytoplasm. This allows nuclear-cytoplastic ratios to be determined by the ratio of green to red fluorescence. Such measurements will enable the determination of the relative number of cells in the proliferation state of the cell cycle. The S and $G_2$ phases are determined by a higher nuclear cytoplastic ratio or higher ratios of green to red fluorescence due to DNA synthesis in the nucleus during the cell doubling process than in non-proliferating cells. The dual-color cells are plated in 96-well dishes and the intensity and ratio of red and green fluorescence determined at various times. By means of this ratio, the status in the cell cycle may be determined.

As with observation of proliferation per se, the assay can be adapted to test the results of treating these cells with various compounds. In this application, control cells are plated in one set of wells and test agents in other sets. Plates are then put in a fluorescence reader capable of dual wavelength measurements to measure the relative increase in green and red fluorescence and their ratio. This will enable the determination of relative proliferation rates as well as on cell cycle position and effects of drugs on these processes.

The heterogeneity of any tissue from which the cells are derived can also be accounted for in the present method by utilizing minimal number of cells per well.

The following examples are intended to illustrate but not to limit the invention. In all cases, images were captured directly with a Hamamatsu C5810 3CCD camera (Hamamatsu Photonics, Bridgewater, N.J.). For macro-imaging, a fluorescence light box (Lightools Research, Encinitas, Calif.) was used. For micro-imaging, a Leica fluorescence stereo microscope model LZ12 was coupled with the CCD camera. This microscope was equipped with a GFP filter set and a mercury lamp with a 50-W power supply. Images were processed for contrast and brightness and analyzed with the use of Image ProPlus 3.1 software. 1024×724 pixel high-resolution images were captured directly on an IBM PC 40).

Preparation A

Production of RFP Retrovirus

For RFP retrovirus production 22), The Hind III/Not I fragment from pDsRed2 (CLONTECH Laboratories, Inc., Palo Alto, Calif.), containing the full-length red fluorescent protein cDNA, was inserted into the Hind III/Not I site of pLNCX2 (Clontech) that has the neomycin resistance gene to establish the pLNCX2-DsRed2 plasmid. PT67, an NIH3 T3-derived packaging cell line, expressing the 10 A1 viral envelope, was purchased from CLONTECH Laboratories, Inc. PT67 cells were cultured in DME medium (Irvine Scientific, Santa Ana, Calif.) supplemented with 10% heat-inactivated fetal bovine serum (FBS) (Gemini Bio-products, Calabasas, Calif.). For vector production, PT67 cells, at 70% confluence, were incubated with a precipitated mixture of LipofectAMINE™ reagent (Life Technologies, Grand Island, N.Y.), and saturating amounts of pLNCX2-DsRed2 plasmid for 18 hours. Fresh medium was replenished at this time. The cells were examined by fluorescence microscopy 48 hours post-transduction. For selection of a clone producing high amounts of a RFP retroviral vector (PT67-DsRed2), the cells were cultured in the presence of 200–1,000 µg/ml of G418 (Life Technologies) for seven days. In some cases, after 15 days of drug selection, surviving colonies were checked under fluorescence microscopy and GFP or RFP-positive colonies were isolated. Several clones were selected and expanded into cell lines after virus titer test by use of 3T3 cell line.

Preparation B

Production of Histone H2B-GFP Vector

For histone H2B-GFP retrovirus production, the histone H2B gene was kindly provided by professor Geoff Wahl (Salk Institute). This gene has no stop codon, enabling the ligation of the H2B gene to the 5' coding region of the *Aequoria victoria* EGFP gene (Clontech) 24). Then this histone H2B-GFP fusion gene was inserted at the Hind III/Cal I site of the pLHCX (Clontech) that has the hygromycin resistant gene. To establish a clone producing high amounts of a histone H2B-GFP retroviral vector, the pLHCX histone H2B-GFP plasmid was transfected to PT67 cells by same method for PT67-DsRed2. The transfected cells were cultured in the presence of 200–400 µg/ml of hygromycin (Life Technologies) for fifteen days and finally PT67-histone H2B-GFP cells were established. In some cases, after 15 days of drug selection, surviving colonies were checked under fluorescence microscopy and GFP or RFP-positive colonies were isolated. Several clones were selected and expanded into cell lines after virus titer test by use of 3T3 cell line.

EXAMPLE 1

Human Prostate Cancer Cells-Expressing Histone H2B-GFP in the Nucleus and pLNC DsRed in the Cytoplasm Dual color PC-3 cells were isolated that express GFP exclusively in the nucleus due to fusion of GFP with histone H2B (21) and express RFP exclusively in the cytoplasm. These cells demonstrate the feasibility of dual color imaging of live prostate cancer cells.

Step I: Preparation of DsRed-Expressing Cells.

PC-3 cells were transformed with pLNC DsRed-2 which is produced from PT67 packaging cells. The DsRed-s expression in the PC-3 cells was monitored under fluorescence microscopy. Selection was with increasing amounts of G418.

Step II: Preparation of Dual Labeled H2B GFP and DsRed-2 Cells.

The DsRed-2 PC-3 cells were transfected with pLHC H2B-GFP DNA using LipofectAMINE Plus™. After 24 hours incubation, the H2B GFP and DsRed-2-expressing cells were selected by increasing amounts of both hygromycin and G418.

Cell-cycle position in living cells is analyzed by the area ratio of the green nucleus to the red cytoplasm. Apoptosis is determined by nuclear morphology in living cells.

EXAMPLE 2

RFP and Histone H2B-GFP Gene Transduction of Fibrosarcoma Cells

For RFP and histone H2B-GFP gene transduction, 70% confluent HT-1080 cells, derived from human fibrosarcoma and were purchased from American Type Culture Collection (Rockville, Md.). To establish dual-color cell, clones of HT-1080 expressing RFP in the cytoplasm (HT-1080-RFP), was established initially. Briefly, HT-1080 cells were incubated with a 1:1 precipitated mixture of retroviral supernatants of PT67-RFP cells and RPMI 1640 (Mediatech, Inc., Herndon, Va.) containing 10% fetal bovine serum for 72 hours. Fresh medium was replenished at this time. Cells were harvested by trypsin/EDTA 72 hours post-transduction and subcultured at a ratio of 1:15 into selective medium, which contained 200 µg/ml of G418. The level of G418 was increased stepwise up to 800 µg/ml. HT-1080-RFP were isolated with cloning cylinders (Bel-Art Products, Pequannock, N.J.) using trypsin/EDTA and amplified by conventional culture methods.

Two cloned sub-lines (HT-1080-dual-1 and HT-1080-dual-6) stably expressed GFP in the nucleus and RFP in cytoplasm. Additional clones containing only RFP or GFP were obtained as controls (HT-1080-RFP, HT-1080-GFP).

EXAMPLE 3

Cell Proliferation Rates of Parental HT-1080-RFP and HT-1080-Dual Clones

Each fluorescent-tagged HT-1080 clone (HT-1080-RFP, HT-1080-dual-1 or HT-1080-dual-6) and parental clone (HT-1080) was seeded at a density of $1 \times 10^3$ cells/dish in 100 mm dishes with RPMI with 10% FBS medium (day 1). The dishes were kept in an incubator at 37° C. and 5% $CO_2$. Every other day (days 2–7), three dishes for each clone were used for cell counts. Briefly, resuspended cells collected after trypsinization were stained with trypan blue (Sigma). Only viable cells were counted with a hemocytometer (Reichert Scientific Instruments, Buffalo, N.Y.) subsequently.

Figure 2:
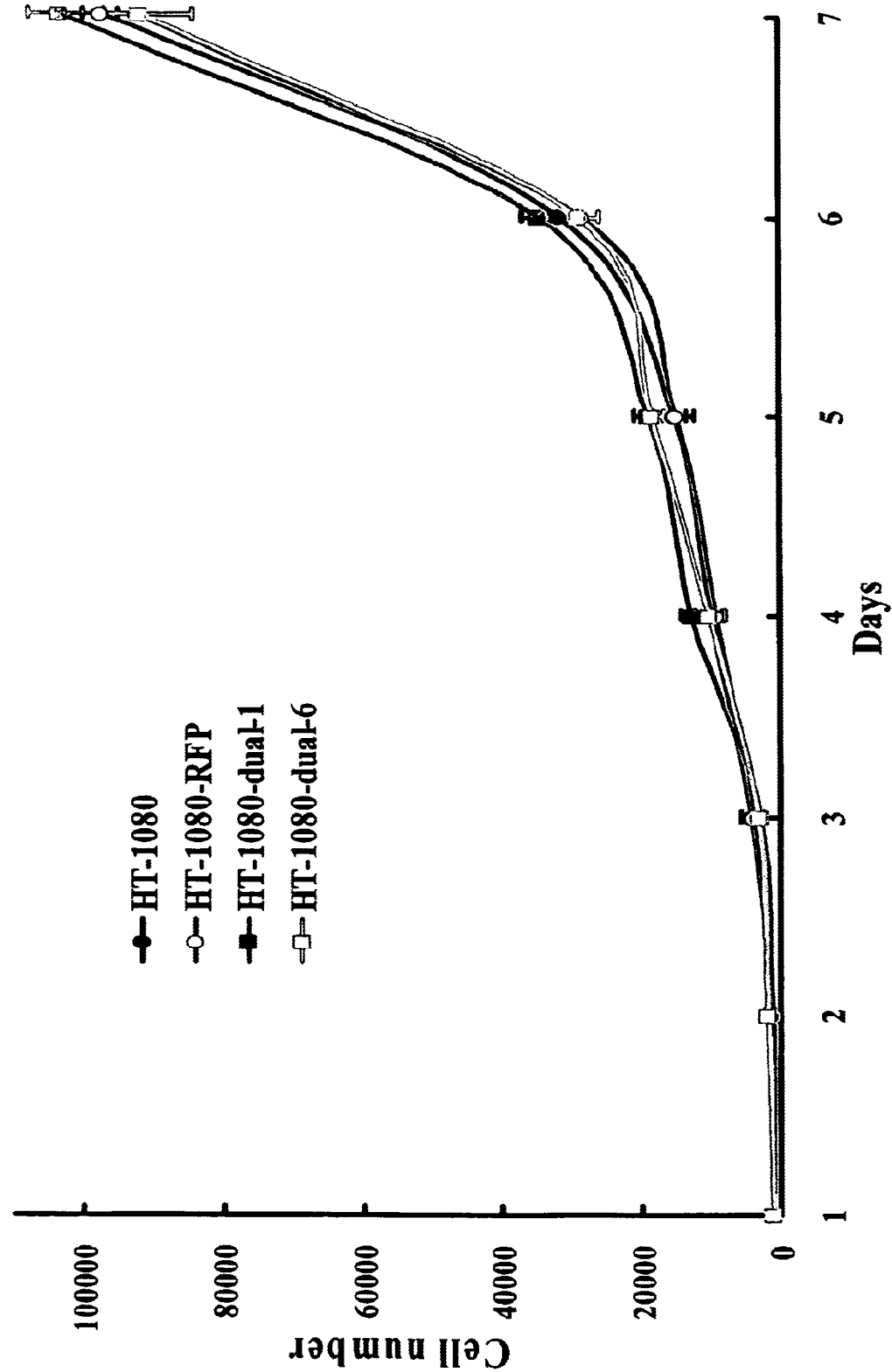
FIG. 2 is a comparison of cell proliferation rates of parental and fluorescent protein expressing clones. Three dishes for each clone (parental HT-1080, HT-1080-RFP, HT-1080-dual-1 and HT-1080-dual-6) were used at each time-point to count the cell number for one week. Cells were trypsinized, stained with trypan blue, and counted in a hemocytometer. Filled circle shows averaged cell number for each group.

FIG. 1 shows the selected HT-1080-dual-color cells have bright GFP and RFP fluorescence in vitro. Green fluorescence is well localized in the nuclei. All cells in the population expressed GFP and RFP, indicating stability of the transgene. FIG. 2 shows there was no difference in the proliferation rates of parental HT-1080, HT-1080-RFP, HT-1080-dual-1 or HT-1080-dual-6 clones determined in monolayer culture.

The HT-1080-dual-1 cells were cultured in 150 mm dishes with RPMI 1640 medium with 10% FBS. Every 5–30 minutes, the dishes were set under fluorescence stereo microscope and time-course images were captured from the same living cells.

Figure 3A:
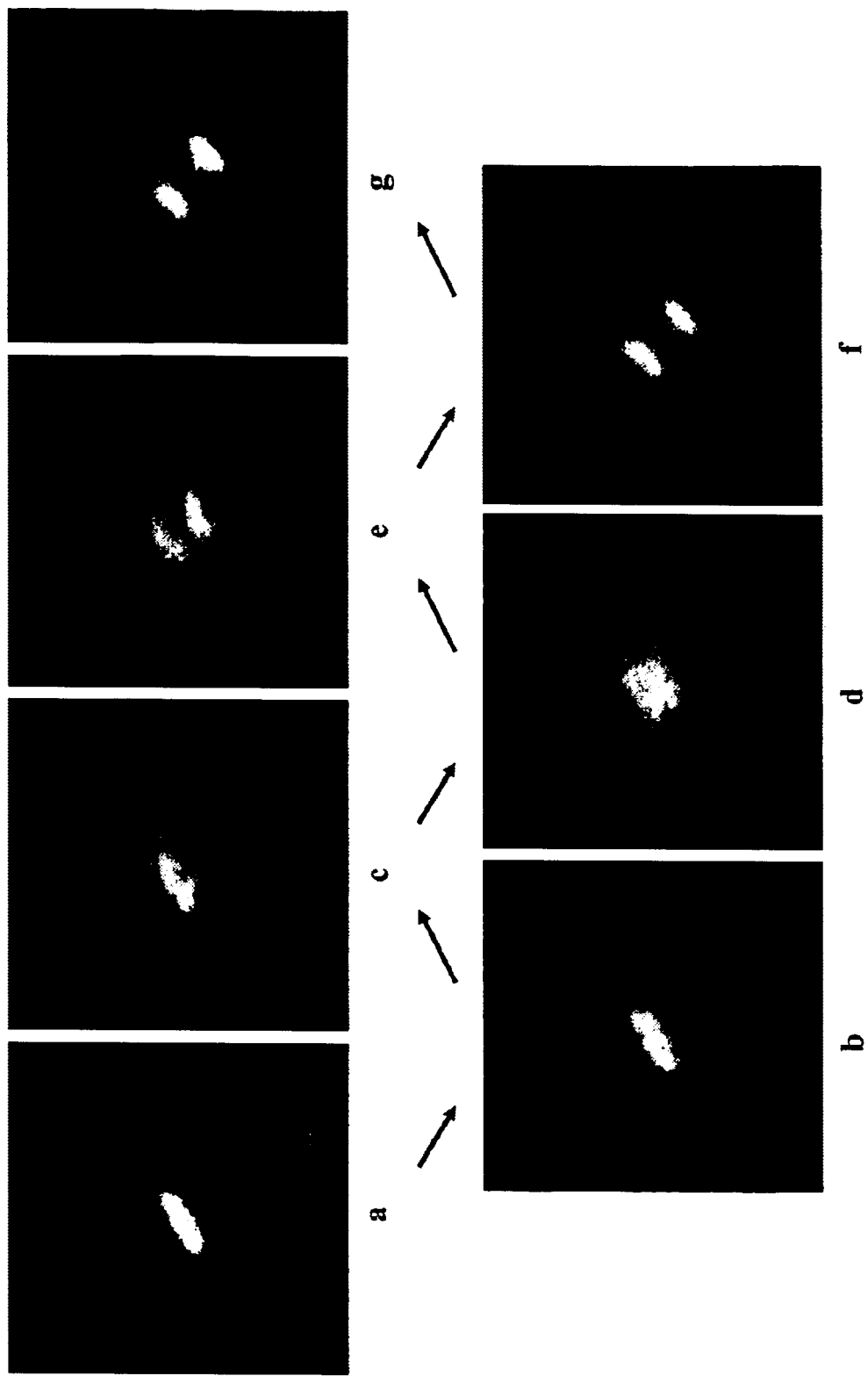
FIGS. 3A–3B show time-course observation of cell proliferation process in vitro using fluorescent labeled cells. HT-1080-dual-1 cells were cultured in PRMI 1640 supplemented with 10% FBS and time-course images were captured from the same living cells under fluorescence microscopy at various time points.
Figure 3B:
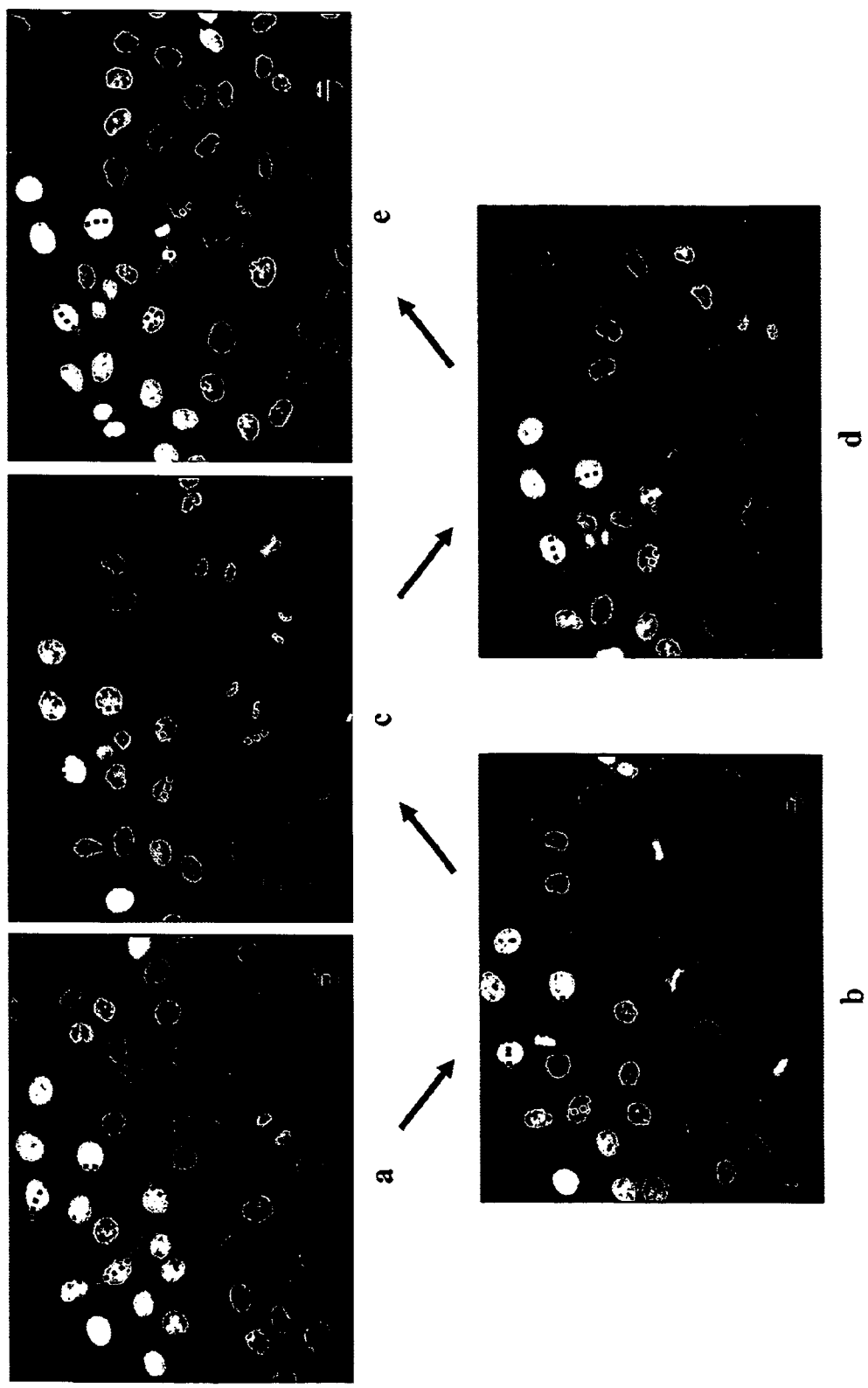

FIG. 3A shows a time-course series of images of HT-1080 dual-1 during mitosis at 5-minute intervals. FIG. 3B shows mitotic cells at 30-minute intervals, where mitotic cells could readily be followed even if they changed position in a large population.

EXAMPLE 4

Real Time Observation of Apoptotic Process In Vitro

To capture the images of real time apoptotic processes, the HT-1080-dual-6 clone was used. Staurosporine (Alexis, San Diego, Calif.), dissolved in DMSO and stored at −80 degrees, was used for induction of apoptosis. $3\times10^5$ cells were seeded in a 25 cm² flask with RPMI 1640 with 10% FBS. Staurosporine was added the next day at a concentration of 2 µM. Every 2 hours, the flask was set under the fluorescent stereo microscope and real time images were captured at each time point.

Figure 4A:
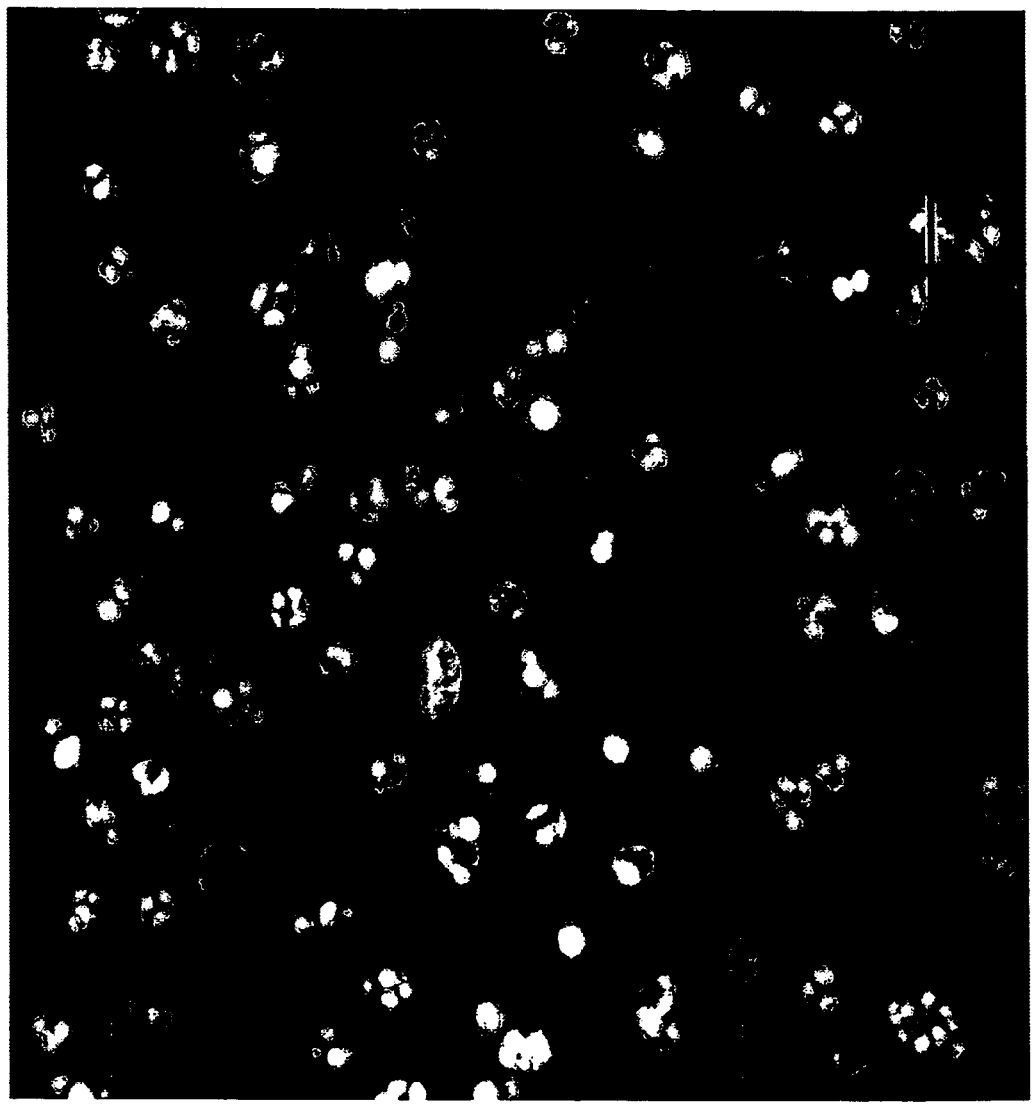
FIGS. 4A–4B show images of HT-1080-dual-6 apoptosis induced by staurosporine. HT-1080-dual-6 cells were incubated with 2 μM staurosporine for apoptosis induction. The cells were visualized under blue light and images were captured with a CCD camera and fluorescence microscope.
Figure 4B:
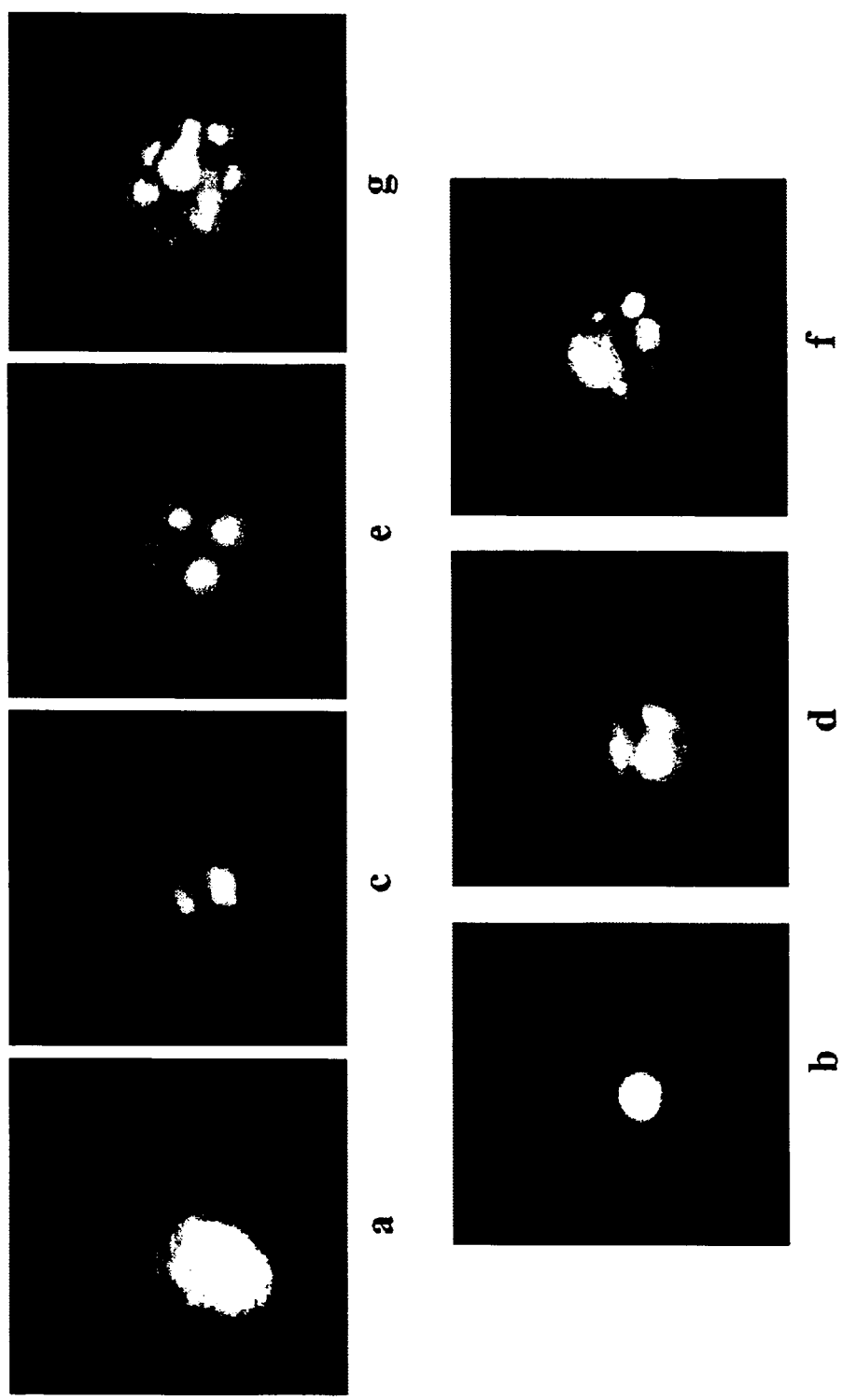

Staurosporine 2 µM induced apoptosis in HT-1080-dual-6 cells. (FIGS. 4A and 4B). Progressive fragmentation of nucleus could be observed every two hours.

EXAMPLE 5

Real Time Observation of Dual-Labeled Cells In Vivo

All animal studies were conducted in accordance with the principles and procedures outlined in the National Institutes of Health Guide for the Care and Use of Laboratory Animals under assurance of number A3873-1. Animals were kept in a barrier facility under HEPA filtration. Mice were fed with autoclaved laboratory rodent diet (Teckland LM-485, Western Research Products, Orange, Calif.).

For cell injection in the common carotid artery, nude mice were anesthetized with a ketamine mixture (ketamine HCl 10 µl, xylazine 7.6 µl, acepromazine maleate 2.4 µl, $H_2O$ 10 µl) via subcutaneous injection. At first, a longitudinal skin incision was made on the neck. After the detecting submandibular gland, it was cut at the middle part and retracted to each side. The right sternohyoid muscle and right sternomastoideus muscle and connective tissue were separated with a blunt instrument. After detection of the right common carotid artery, the artery was gently released from surrounding connective tissue. Light tension was put on the proximal site of artery with a blunt-end hook (Fine Science Tools, Inc., Foster City, Calif.). A total of 200 µl of medium containing $2\times10^5$ HT-1080-dual-1 cells was injected in the artery by using 33G needle (Fine Science Tools). Immediately after the injection, the injected site was pressed with a swab to prevent bleeding or leakage of injected tumor cells for a while. After confirmation of arrest of bleeding, the skin was closed with a 6-0 suture. All procedures of the operation described above were performed with a 7× dissection microscope (MZ6, Leica, Deerfield, Ill.).

Figure 5:
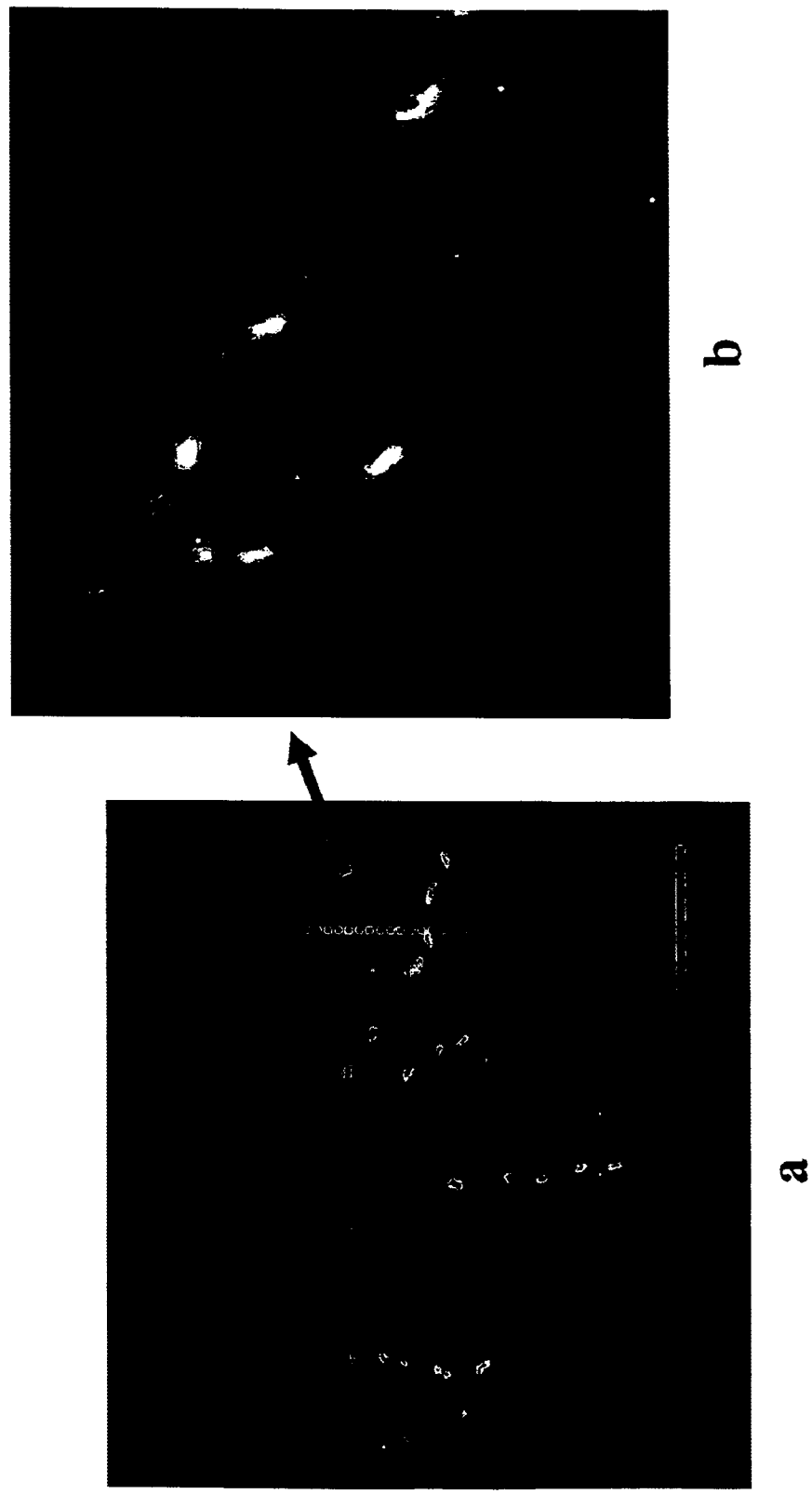
FIGS. 5A–5B show brain experimental metastases immediately after injection of HT-1080-dual-1 cells into the common carotid artery. Emboli of dual-coded cells in micro arteries were observed at the single cell level through the skull with skin flap window. The cell morphology and the morphology of the nuclei of each cell are visualized.

After common carotid-artery injection of HT-1080-dual-1, embolic cells in a brain micro-artery were visualized even through the skull via a scalp flap (FIGS. 5A and 5B). The skull of the mouse is relatively transparent. The tumor cells were observed to have elongated to adapt to the microvessels similar to leukocytes. The nuclei of tumor cells were very elongated in the tumor cells visualized in the vessels.

EXAMPLE 6

Visualizing Nucleus-Cytoplasmic Dynamics of Tumor Cells In Vivo

To visualize tumor cells nuclear cytoplasmic dynamics in vivo, mice were anesthetized with ketamine mixture. The surfaces of ears were directly observed by fluorescence stereo microscope under blue light.

To observe nucleus cytoplasmic dynamics in lung metastasis, six nude mice were injected with $1\times10^6$ HT-1080-dual-1 cells at the volume of 300 µl in the tail veins. At various time points, mice were sacrificed and lungs were removed. The metastatic colonies on the lung were visualized directly under blue light. For histological analysis, the excised lungs were embedded with tissue frozen medium (Triangle Biomedical Sciences, Durham N.C.) and stored at −80 degrees. Frozen sections were prepared by cryostat LEICA model CM-1850 at the thickness of 4 µm. The prepared sections were directly observed under fluorescence stereo microscope with GFP filter set.

Micrometastases on excised lungs were visualized with each nucleus in close proximity to each other (data not shown). The cells appear to be distorted to enable contact between nuclei.

This study opens up the possibility of real time observation of tumor cell nuclear-cytoplasmic dynamics including apoptotic process at the cellular level in vivo as well as in vitro. Mitotic cells were readily visualized after injection in the mouse ear in live mice. After tail-vein injection, dual-color micrometastases were visualized in excised lungs.

EXAMPLE 7

Whole Body Fluorescent Optical Imaging

Figure 6:
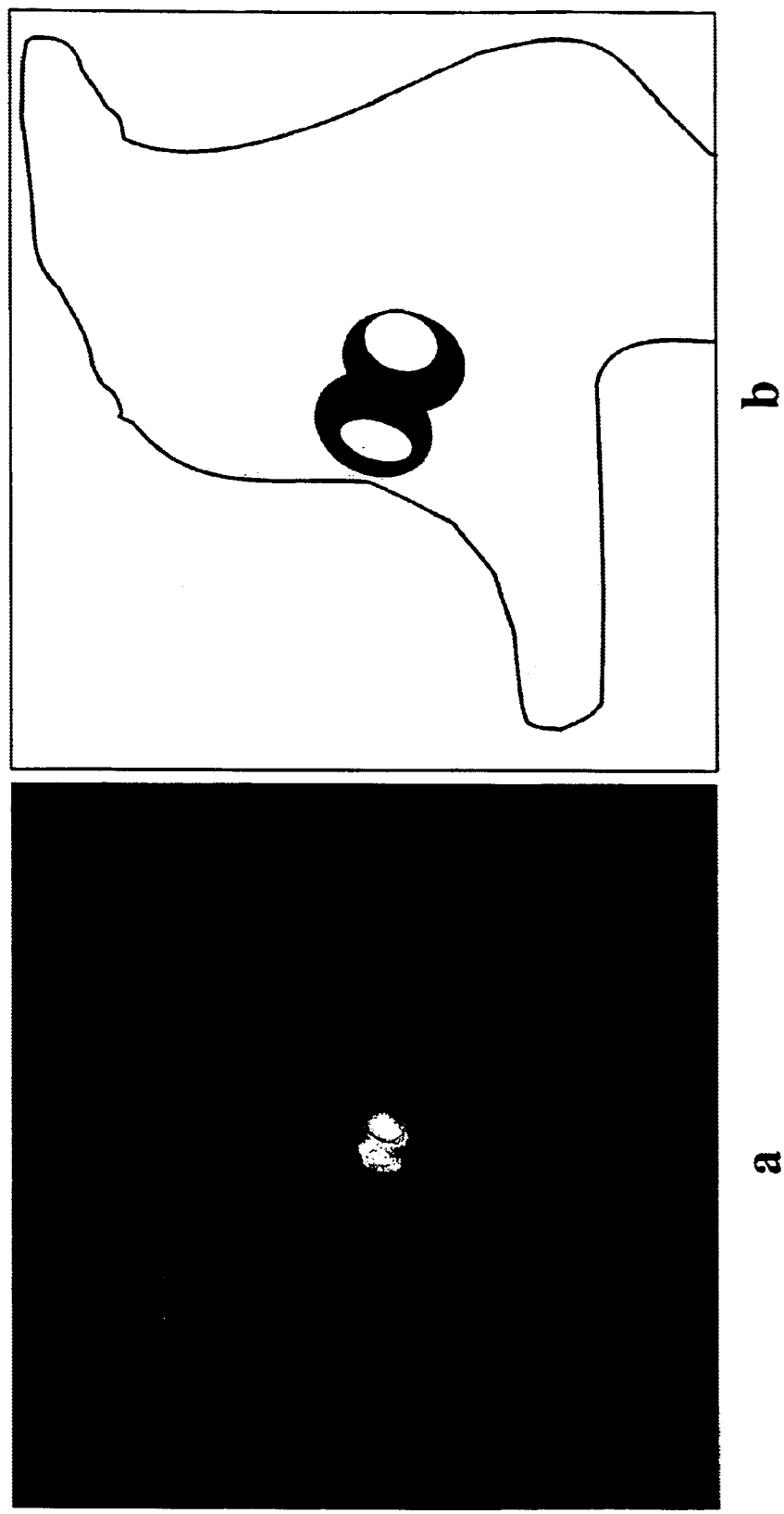
FIGS. 6A–6B show real time image of tumor cell proliferation on living mouse. Real time image of mitotic tumor cells in live mouse was captured 12 hours after the cells injection.
Figure 7:
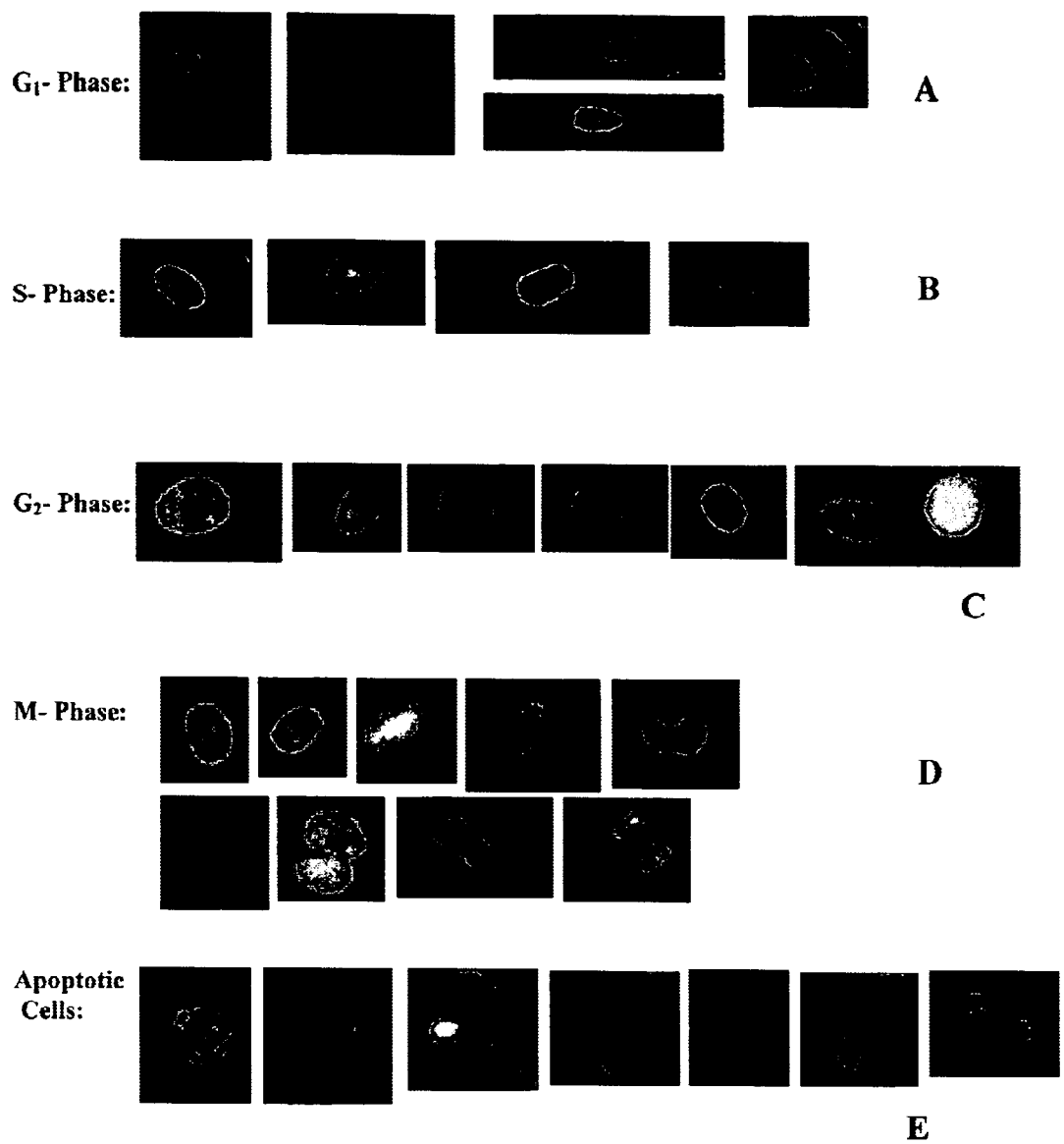
FIGS. 7A–7D show images of the cell cycle of dual labeled PC-3 human prostate cancer cells, including $G_1$-phase, S-phase, $G_2$-phase and M-phase.
FIG. 7E shows PC-3 dual labeled cells undergoing apoptosis.

Real time images of mitotic cells could be captured in the living mouse 12 hours after the injection of HT-1080-dual-1 (FIGS. 6A and 6B). The cells shown seemed to be extravasated and appear rounded, similar to dividing cells in culture. The conditions of each nucleus and the boundary of the cells were visualized in the living animal without any fixation or staining.

EXAMPLE 8

Preparation of a Dual-Colored Human Prostate Cancer Cell Line

PC-3 cells were grown in RPMI1640 medium supplemented with 10% FCS. Exponentially growing cells (in 10 cm dishes) were incubated with the viral supernatants from PT67/pLHCX H2B-EGFP in the presence of 8 µg ml$^{-1}$ Polybrene. After overnight incubation, medium was changed, and the infected cells were expanded for step-wise Hygromycin selection. After 15 days of drug selection, surviving colonies were visualized under fluorescence microscopy, and GFP-positive colonies were isolated. A clone with uniform, high-level expression of H2B-EGFP was selected.

Exponentially growing H2B-EGFP expression cells were then incubated with the viral containing supernatants from PT67/pLNCX DsRed-2 in the presence of 8 µg/ml Polybrene. After overnight incubation medium was changed and the infected cells were expanded for step-wise G418 selection after 48 hours infection. After 15 days of drug selection, surviving colonies were visualized under fluorescence microscopy and RFP-positive colonies were isolated. A clone with uniform, high-level expression of both H2B-EGFP and RFP (PC3-dual) was selected.

For growth rate determination, $1\times10^5$ cells were cultured in 60 mm Petri dishes and counted every day for one week. The number of viable cells/well was determined at the indicated times in triplicate, excluding dead cells by trypan blue staining.

The high expression of H2B-EGFP and cytoplasm RFP in this cell line was stable for more than three months in the absence of Hygromycin B and G418 selection culture. The proliferation rate of the dual-colored cells is same as its parental cell PC-3 in vitro. These results indicate that dual-colored PC-3 could be a useful model for in vivo and in vitro studies.

EXAMPLE 9

Observation of Cell Cycle and Apoptosis

The dual-color cells could be easily placed in their cell cycle position by the "nuclear-cytoplasmic" ratio as observed in living cells. For fluorescence microscopy of these cells, a Leica fluorescence stereo microscope model LZ12 equipped with a mercury 50W lamp power supply was used. To visualize both GFP and RFP fluorescence at the same time, excitation was produced through a D425/60 band pass filter, 470 DCXR dichroic mirror, and emitted fluorescence was collected through a long pass filter GG475 (Chroma Technology, Brattleboro, Vt.).

FIGS. 7A–7D show the cell cycle phases; FIG. 7E shows apoptosis.

The large nuclear size compared to the cytoplasm readily identified $G_2$-phase cells compared to $G_1$-phase cells with much smaller nuclear-cytoplasm ratios. The S-phase cells had nuclear-cytoplasmic ratios larger than $G_1$ but smaller than $G_2$. Prophase cells about to enter mitosis were identified by chromosome condensation. Cells with the metaphase plate lined up were readily observed and could be visualized as they entered anaphase. Apoptotic cells were identified by an aberrant nuclear morphology including fragmentation.

Thus, sequential cell cycle progression of individual cells could be followed in real time with photo micrographs taken at frequent intervals.

EXAMPLE 10

Real-Time Visualization of Drug-Induced Apoptosis

Figure 8:
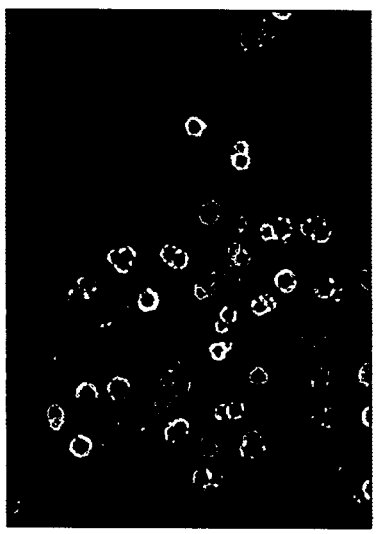
FIG. 8 shows the time course of effect of Taxol™ on PC-3 dual labeled cells.
Figure 8:
Figure 8:
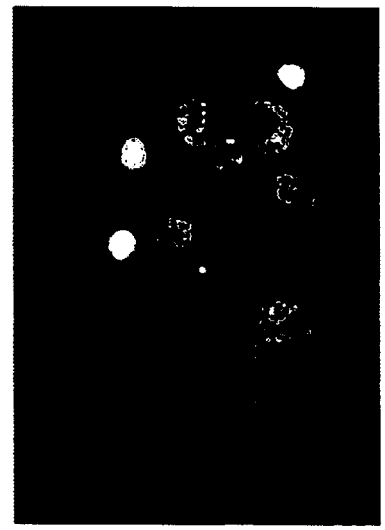

PC-3 dual cells were treated with Taxol™ (0.8 ug/ml); thymidine (2 mM), and vinblastine (60 nM). Real-time imaging was done at 0, 12, 24, 36, and 48 hours. Cells were collected for DNA extraction and agarose gel electrophoresis (1.8%) analysis. Paclitaxel (Taxol™) (0.8 $\mu$g/ml) had very specific effects on the nuclei causing them to form a ring-shaped structure apparently due to the attachment of the chromatin to the nuclear membrane. FIG. 8 shows this was readily visible with the GFP-labeled nuclei against the background of the RFP-labeled cytoplasm. The nuclear ring structures were viable by 24 hours. By 48 hours, the cells could be seen entering apoptosis with very aberrant nuclear structures and fragmentation.

Figure 9:
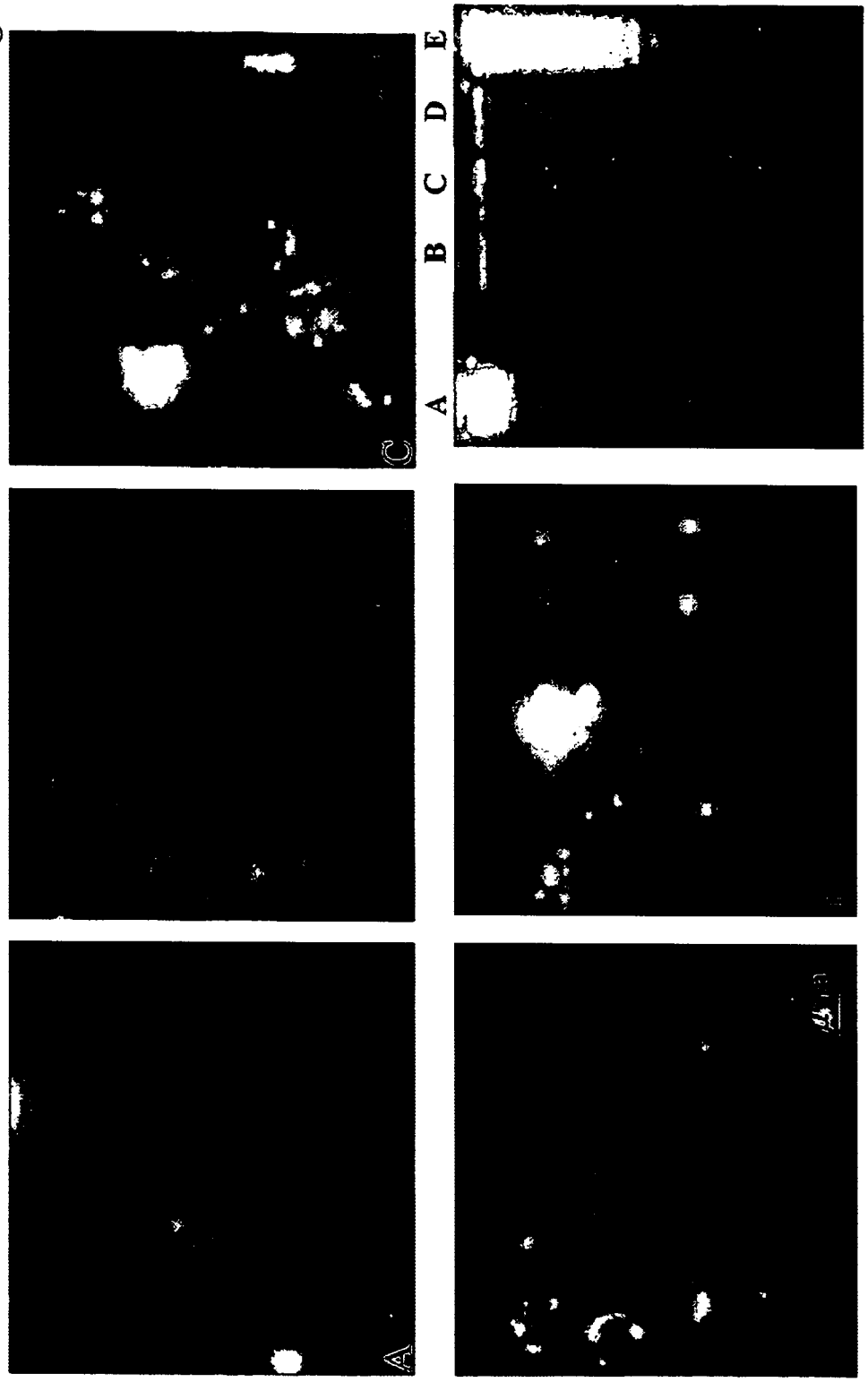
FIG. 9 shows alternative imaging of the effect of Taxol™, including the results shown in gel electrophoresis.

FIG. 9 shows that the ring structures induced by Taxol™ observed at 24 hours after initiation of treatment was before DNA fragmentation occurred and could be observed by gel electrophoresis. By 48 hours, when the cells were well into apoptosis, DNA fragmentation could be observed.

Figure 10:
FIG. 10 shows the effect of the treatment of vinblastin on dual labeled PC-3 cells.
Figure 10:
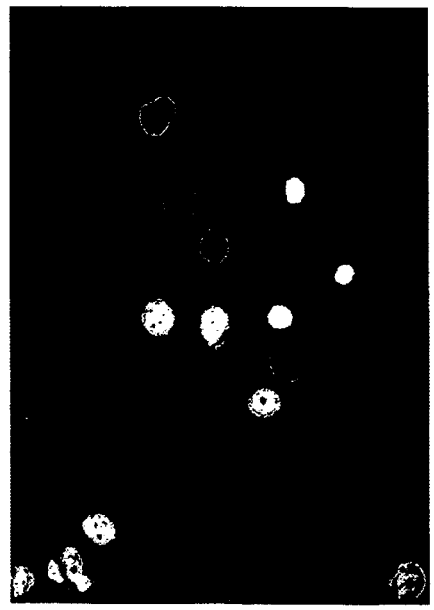
Figure 10:
Figure 10:
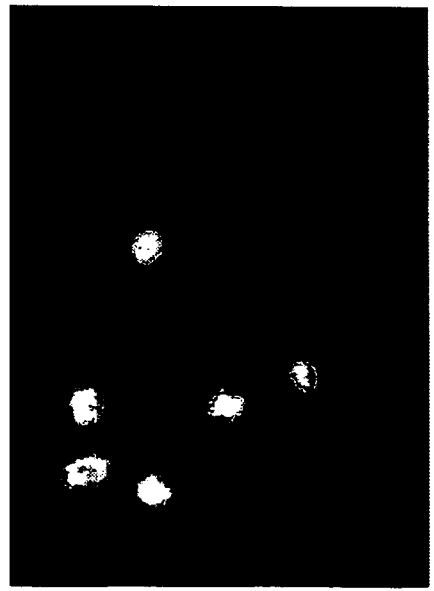

Another tubulin agent, vinblastine (60 nM), had different effects on the cell nuclei as compared to Taxol™, wherein the nuclei became more condensed and the cytoplasm appeared to expand as shown in FIG. 10.

EXAMPLE 11

In Vivo Observation

All animal studies were conducted in accordance with the principles and procedures outlined in the National Institutes of Health (NIH) Guide for the care and use of animals under NIH assurance number A3873-1. Male nude mice (NCr-nu) between 5 and 6 weeks of age were maintained in a barrier facility on HEPA-filtered racks. The dual colored PC-3 human prostate cancer cells were injected ($2 \times 10^6$) into the nude-mouse foot pad. Mice were euthanized after 20 days. Tumor and lymph nodes and lungs were processed for fluorescence microscopy.

Figure 11:
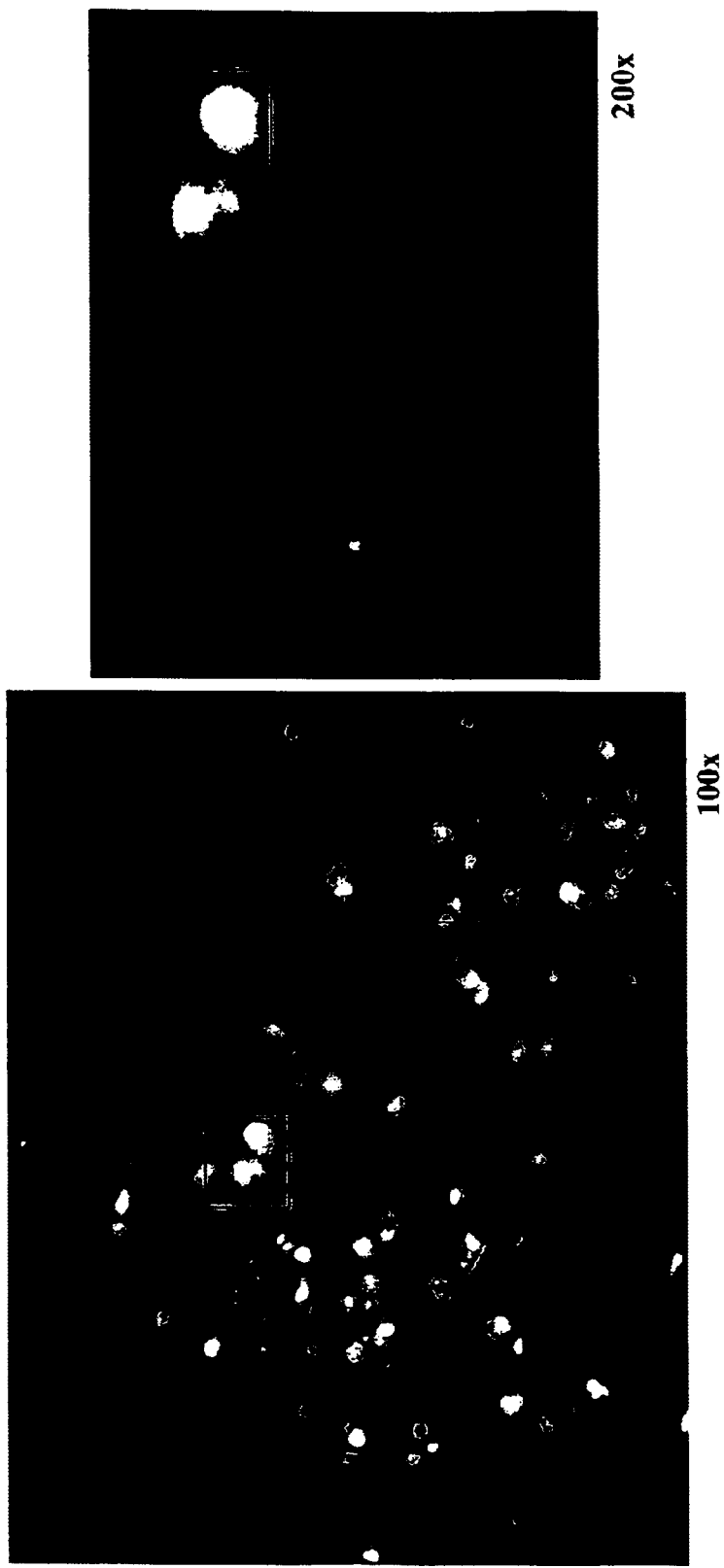
FIG. 11 shows an in vivo image of apoptotic PC-3 dual labeled cells.

FIG. 11 shows mitotic dual-color PC-3 cells were observed in the lymph node under fluorescence microscopy.

What is claimed is:

1. A method to prepare living cells which cells comprise a first fluorescent protein localized to the nucleus and a second fluorescent protein localized to the cytoplasm wherein said first and second fluorescent proteins emit light of different wavelengths which method comprises modifying living cells to contain either (a) a first expression system for expression of said first fluorescent protein wherein said first fluorescent protein is fused to an amino acid sequence which targets said fusion protein to the nucleus and a second expression system for expression of a second fluorescent protein lacking a nucleus targeting sequence; or (b) an expression system that expresses both said first fluorescent protein and second fluorescent protein as described; and selecting said modified cells for cells that have been stably modified.

2. The method of claim 1, wherein in step (a), said cells are first modified with said first expression system and then modified with said second expression system or vice versa.

3. The method of claim 1, wherein in step (a), the cells are modified with both expression systems simultaneously.

4. The method of claim 1, wherein said selecting is by culturing in the presence of an antibiotic or a toxin.

5. A colony of living cells stably modified to produce a first fluorescent protein fused to an amino acid sequence targeting the nucleus and a second fluorescent protein lacking an amino acid sequence targeting the nucleus;

wherein said first and second fluorescent proteins emit visible light at different wavelengths.

6. A colony of living cells which are modified to contain a first fluorescent protein localized to the nucleus and a second fluorescent protein localized to the cytoplasm wherein said first fluorescent protein and second fluorescent protein are of different colors.

7. The colony of claim 6, wherein said first fluorescent protein is green and said second fluorescent protein is red.

8. The colony of claim 5, wherein said amino acid sequence targeting the nucleus is histone H2B.

9. A method to determine the cell cycle position of living cells which method comprises assessing the ratio of nuclear area to cytoplasmic area of the cells of the colony of claim 6.

10. The method of claim 9, wherein said assessing is performed as a function of time.

11. The method of claim 9, wherein said cells of said colony are observed in a living animal.

12. A method to determine the effect of an agent on cells, which method comprises treating a first sample of the colony of claim 6 with said agent and observing the effect of said treating on the distribution and/or intensity of radiation emitted from said colony.

13. The method of claim 12, which further comprises observing the distribution and/or intensity of radiation emitted from a second sample of said colony that has not been treated with said agent, and comparing the observations made on the first sample with those on the second sample.

14. The method of claim 12, wherein the distribution and/or intensity are evaluated for being characteristic of dormancy.

15. The method of claim 12, wherein said distribution and/or intensity are evaluated for being characteristic of apoptosis.

16. The method of claim 12, wherein said distribution and/or intensity are evaluated for being characteristic of stages in the cell cycle.

17. A method to determine the location of an agent as the cytoplasm or nucleus which method comprises treating the colony of claim 6 with said agent and observing the distribution and/or intensity of radiation emitted from the cytoplasm and nucleus.

18. The method of claim 17, wherein said agent itself is labeled, and said method further comprises directly observing the location of the label.

19. A method to determine the proliferation rate of a cell culture which method comprises culturing cells which have been modified to contain a fluorescent protein; and measuring the fluorescence emitted by said cells as a function of time, whereby the rate of proliferation of said cells is determined, as correlated to the rate of increase of intensity of emitted fluorescence.

20. The method of claim 19, wherein said fluorescent protein is a green fluorescent protein (GFP) or a red fluorescent protein (RFP).

21. The method of claim 19, wherein said culture is grown from a single cell.

22. A method to determine the effect of a test compound on cell proliferation which method comprises culturing cells in the presence and absence of said test compound, wherein said cells have been modified to contain a fluorescent protein;

measuring the intensity of fluorescence as a function of time in the presence and absence of said compound so as to determine the rate of proliferation in the presence and absence of said compound, as correlated to the rate of increase of intensity of emitted fluorescence; and comparing the rate of proliferation in the presence and absence of said compound;

wherein a change in the rate of proliferation in the presence as opposed to the absence of said compound identifies said compound as a modulator of cellular proliferation.

23. The method of claim 22, wherein said fluorescent protein is a green fluorescent protein (GFP) or a red fluorescent protein (RFP).

24. The method of claim 22, wherein said culturing is commenced from a single cell.

25. A method to determine the heterogeneity of a tumor, which method comprises culturing a multiplicity of colonies from individual cells or individual groups of cells contained in said tumor; and determining the rates of proliferation of said cell cultures;

whereby cultures exhibiting different rates of proliferation indicate heterogeneity of said tumor.

26. The method of claim 25, wherein said cells have been modified to contain a fluorescent protein and the rates of proliferation are determined, as correlated to the rate of increase of intensity of emitted fluorescence, by measuring the intensity of emitted fluorescence as a function of time.

27. The method of claim 26, wherein said cells have been modified to contain a first fluorescent protein localized to the nucleus and a second fluorescent protein localized to the cytoplasm wherein said first fluorescent protein and second fluorescent protein are of different colors.

* * * * *